United States Patent
Jung et al.

[11] Patent Number: 5,998,649
[45] Date of Patent: Dec. 7, 1999

[54] ORGANOSILICON COMPOUNDS AND METHOD FOR PREPARATION

[76] Inventors: Il Nam Jung, 21-1303 Hyndai Apartmant, Ogum-dong, Songpa-ku, Seoul; Bok Ryul Yoo, 903-303 Lotte Appartment, 1058 Ilsan-3-dong, Ilsan-ku, Koyang-si, Kyunggi; Joon Soo Han, 801-2401 Hyndai Appartment, Kwangjang-dong, Kwangjinku, Seoul 138-130; Weon Cheol Lim, 1-906 Dongin Appartment, Kaebong-dong Kuro-ku, Seoul 152-092, all of Rep. of Korea

[21] Appl. No.: 09/312,900

[22] Filed: May 17, 1999

[51] Int. Cl.$^6$ ........................................................ C07F 7/08
[52] U.S. Cl. ............................................. 556/406; 556/435
[58] Field of Search ........................................ 556/406, 435

[56] References Cited

U.S. PATENT DOCUMENTS

| | | | |
|---|---|---|---|
| 3,159,601 | 12/1964 | Ashby | 260/46.5 |
| 3,220,972 | 11/1965 | Lamoreaux | 260/46.5 |
| 3,296,291 | 1/1967 | Chalk et al. | 260/448.2 |
| 3,419,593 | 12/1968 | Willing | 260/448.2 |
| 3,516,946 | 6/1970 | Modic | 252/429 |
| 3,527,781 | 9/1970 | Levin | 556/406 |
| 3,655,713 | 4/1972 | LeGrow et al. | 556/406 |
| 3,814,730 | 6/1974 | Karstedt | 260/46.5 |
| 3,928,629 | 12/1975 | Chandra et al. | 427/387 |
| 3,989,668 | 11/1976 | Lee et al. | 260/46.5 |
| 5,036,117 | 7/1991 | Chung et al. | 522/172 |
| 5,391,794 | 2/1995 | Jung et al. | 556/435 |
| 5,399,740 | 3/1995 | Jung et al. | 556/435 |
| 5,420,323 | 5/1995 | Jung et al. | 556/415 |
| 5,498,736 | 3/1996 | Tamao et al. | |
| 5,527,934 | 6/1996 | Jung et al. | 556/431 |
| 5,605,991 | 2/1997 | Chamberlain et al. | 526/178 |

OTHER PUBLICATIONS

Han et al., "Direct Synthesis of Tris(chlorosilyl)methanes Containing Si–H Bonds," Organometallics, 1997, 16,93.
Yeon et al., "Effects of Hydrogen Chloride Addition to the Direct Reaction of Methylene Chloride with Elemental Silicon," J. Organomet. Chem. 1996, 516,91.
Watanabe et al., J. Organomet. Chem. 1980, 195, 363.
Polyakova et al., Izv. Akad. Nauk SSSR, Ser. Khim. 1965, 1267.
Tanaka et al., "Platinum–Complex–Catalyzed Dehydrogenative Double Silylation of Acetylenes, Dienes, and Olefins with Bis(hydrosilane) Compounds," Organometallics, 1991, 10, 16.
Speier et al., "The Addition of Silicon Hydrides to Olefinic Double Bonds. Part II. The Use of Group VIII Metal Catalysts," J. Am. Chem. Soc., 1957, 79, 974.

Primary Examiner—Paul F. Shaver
Attorney, Agent, or Firm—William F. Boley

[57] ABSTRACT

The invention is cyclic organosilicon compounds described by formula

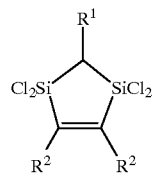

and by formula

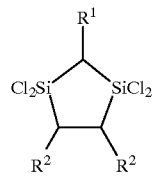

and linear organosilicon compounds by formula

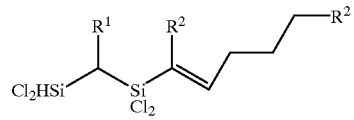

and by formula

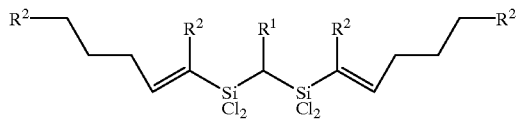

where $R^1$ is selected from the group consisting of hydrogen, dichlorosilyl, trichlorosilyl, methyldichlorosilyl, dimethylchlorosilyl, and trimethylsilyl, and each $R^2$ is independently selected from the group consisting of hydrogen, alkyls comprising one to about 6 carbon atoms, and aryls; and methods for making the described cyclic organosilicon compounds and linear organosilicon compounds.

18 Claims, No Drawings

ORGANOSILICON COMPOUNDS AND METHOD FOR PREPARATION

BACKGROUND OF INVENTION

Since the description of hexachloroplatinic as a catalyst for hydrosilation in 1957 by Speier et al., *J. Am. Chem. Soc.* 1957, 79, 974, hydrosilation has become one of the fundamental mehtods for synthesizing organosilicon compounds. In the hydrosiation process Si—H bond containing silicon compounds are reacted and added to multiple bonds of organic compounds such as carbon—carbon, carbon-oxygen, carbon-nitrogen, nitrogen—nitrogen, and nitrogen oxygen.

In 1980, Watanabe et al., *J. Organomet. Chem.* 1980, 195, 363, reported that when hydridasiane is reacted with acetylene in the presence of a metal catayst such as $RuCl_2(PPH_3)_3$, $PtCL_2(PPh_3)_2$, $RhCl(PPh_3)_3$, $RhH(PPh_3)_4$, or $Pt(PPh_3)_4$, vinylsilane is obained in good yield. The double hydrosilation product of 1,2-bis-silylethane was also obtained as a byproduct.

Polyakova et al., *Organometallics* 1991, 10, 16, reported platinum complex catalyed dehydrogenative double silation of unsaturated hydrocarbons with bis(hydrosilane) compounds Tanaka et al. examined various catalysts such as $Pt(CH_2=CH_2)(PPh_3)_2$, $PtCl_2(PPh_3)_2$, $Ru_3(CO)_{12}$, $Pd(dba)_2$ $PPh_3$, $RhCl(PPh_3)_3$, $PdCl_2(PPh_3)_2$, and $Pd(PPh_3)_4$.

Jung et al., U. S. Pat. No. 5,399,740, describe the reaction of silicon metal with a mixture of a dichloromethyl group containing silane and hydrogen chloride to obtain tris(silyl)methanes in moderately high yield.

Han et al., *Organometallics* 1997, 16, 93, reported the direct synthesis of Si—H containing tris(silyl)methanes by reacting silicon metal with a mixture of chloroform and hydrogen chloride.

Yeon et al., *J Organomet. Chem.* 1996, 516, 91, reported the direct synthesis of Si—H containing bis(silyl)methanes by reacting silicon metal with a mixture of methylene chloride and hydrogen chloride.

The organosilicon compounds of the present invention are useful, for example, as intermediates for forming silicon carbides by pyrolysis.

SUMMARY OF INVENTION

The present invention is cyclic organosilicon compounds described by formula

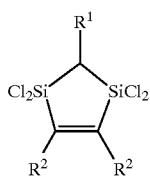

and by formula

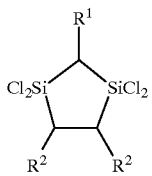

and linear organosilicon compounds described by formula

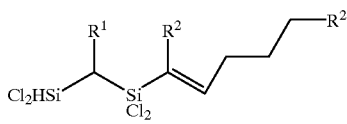

and by formula

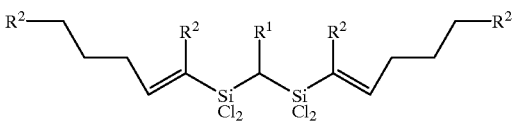

where $R^1$ is selected from the group consisting of hydrogen, dichlorosilyl, trichlorosilyl, methyldichlorosilyl, dimethylchlorosilyl, and trimethylsilyl, and each $R^2$ is independently selected from the group consisting of hydrogen, alkyls comprising one to about 6 carbon atoms, and aryls; and methods for making the described cyclic organosilicon compounds and linear organosilicon compounds.

DESCRIPTION OF INVENTION

The present invention is cyclic organosilicon compounds described by formula (1)

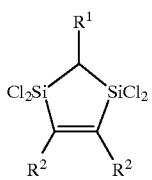

and by formula (2)

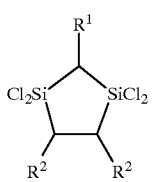

and linear organosilicon compounds described by formula (3)

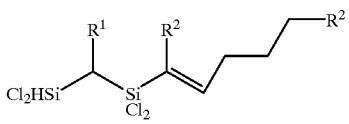

and by formula (4)

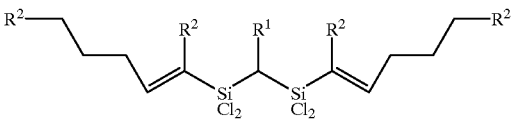

where $R^1$ is selected from the group consisting of hydrogen, dichlorosilyl, trichlorosilyl, methyldichlorosilyl, dimethylchlorosilyl, and trimethylsilyl, and each $R^2$ is independently selected from the group consisting of hydrogen, alkyls comprising one to about 6 carbon atoms, and aryls; and methods for making the cyclic organosilicon compounds described by formulas (1) and (2) and linear organosilicon compounds described by formulas (3) and (4).

In formulas (1), (2), (3), and (4) $R^2$ can be, for example, hydrogen, methyl, ethyl, propyl, n-butyl, t-butyl, hexyl, phenyl, and tolyl. It is preferred that each $R^2$ be independently selected from the group consisting of hydrogen and methyl. Examples of organosilicon compounds which can be made by the present method are found in the Examples provided herein.

The present invention is also a method for making cyclic organosilicon compounds described by formulas (1) and (2) and linear organosilicon compounds described by formulas (3) and (4). The method comprises effecting hydrosilation of a a bis(dichlorosilyl)methane described by formula (5)

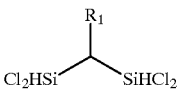

with an alkyne described by formula (6)

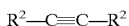

in the presence of an effective amount of metallic hydrosilation catalyst, where $R^1$ is selected from the group consisting of hydrogen, dichlorosilyl, trichlorosilyl, methyldichlorosilyl, dimethylchlorosilyl, and trimethylsilyl, and each $R^2$ is independently selected from the group consisting of hydrogen, alkyls comprising one to about 6 carbon atoms, and aryls.

Examples of the bis(dichlorosilyl)methane include bis(dichlorosilyl)methane, bis(dichlorosilyl)trichlorosilylmethane, bis(dichlorosilyl)dichloromethylsilylmethane, and tris(dichlorosilyl)methane. Preferred examples of the bis(dichlorosilyl)methane include bis(dichlorosilyl)trichlorosilylmethane and tris(dichlorosilyl)methane.

The $R^2$ substituents of the alkyne described by formula (6) can be any of those groups described above for $R^2$ and can be the same or different. Preferred is when $R^2$ is selected from the group consisting of hydrogen and phenyl. The alkyne can be for example acetylene, phenylacetylene, and diphenylacetylene.

The mole ratio of the alkyne to the bis(dichlorosilyl)methane added to the method can be within a range of about 0.1 to 10. It is preferred that the mole ratio of the alkyne to the bis(dichlorosilyl)methane be greater than about 0.8, with a mole ratio within a range of about 1 to 2 being most preferred.

The present method requires the presence of an effective amount of a metallic hydrosilation catalyst. The metallic hydrosilation catalyst can be any such catalyst which is known to catalyze the reaction of silicon-bonded hydrogen atoms with alkyne groups. The referred metallic hydrosilation catalyst for use in the present method are platinum group metal-containing catalyst. By "platinum group metal" it is meant ruthenium, rhodium, palladium, osmium, iridium, and platinum. Examples of platinum group metal-containing catalyst which may be useful in the present method are found in, for example, Willing, U.S. Pat. No. 3,419,593; Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalyst and methods for their preparation. A preferred platinum group metal is platinum. The preferred platinum group metal catalysts are compounds and complexes of platinum. Examples of metallic hydrosilation catalysts which may be useful in the present method include $H_2PtCl_6$, $H_2PtCl_6$ in solution in isopropyl alcohol (IPA), $H_2PtCl_6/IPA/PPh_3$ solutions, $H_2PtCl6/THF$ (tetrahydrofuran) solutions, $H_2PtCl_6/I_2$, $Pt((CH_2=CHSiMe_2)_2O)_2$, $RhCl(PPh_3)_3$, $Pt(CH_2=CH)(PPh_3)_2$, $Pd(PPh_3)_4$, $Pt(PPh_3)_4$, and $Ni(PEt_3)_4$, where Et is ethyl and Ph is phenyl.

The present method requires that an effective amount of a metallic hydrosilation catalyst be added. By the term "effective amount" it is meant an amount of catalyst sufficient to accelerate a reaction between the silicon-bonded hydrogen atoms of the bis(dichlorosilyl)methane and the alkyne. Generally, an effective amount of the metallic hydrosilation catalyst is an amount within a range of about $1\times10^{-5}$ to 0.05 moles of metal per mole of the bis(dichlorosilyl)methane added to the method.

The method of effecting hydrosilation of the bis(dichlorosilyl)methane with the alkyne can be any of those known methods for effecting hydrosilation reactions in the presence of a metallic hydrosilation catalyst. In a preferred process an optional organic solvent, the bis(dichlorosilyl)methane, and the metallic hydrosilation catalyst are placed in a reactor under an inert atmosphere such as dried nitrogen. The alkyne is then slowly added to the reactor with stirring. After addition of the alkyne, the reactor content may be further heated at a temperature from about 10° C. to 150° C. for a time sufficient to ensure completion of the hydrosilation reaction. It is preferred to heat the reactor content at a temperature within a range of about 20° C. to 150° C., and even more preferred is a temperature of about 80° C. to 110° C. The length of time the reactor content is heated to effect the hydrosilation reaction will depended upon the reactants and the temperature to which the reactor content is heated. Generally a time of about 0.5 hours to 20 hours is useful, with a heating time of about 1 hour to 5 hours being preferred.

The use of an organic solvent in the present method is optional. Organic solvents which may be useful in the present method include benzene, toluene, xylene, chlorobenzene, and anisole. The organic solvent may be added to the method as a diluent in any amount that preferably does not dilute the reactants to a point that detrimentally effects the reaction rate and yield.

The following examples are provided to illustrate the present invention. These examples are not intended to limit the scope of the claims herein.

EXAMPLE 1

Hydrosilation of acetylene with bis(dichlorosilyl) trichlorosilylmethane in the presence of $H_2PtCl_6$. To a 50 ml, three-necked, dried, flask equipped with a magnetic stirrer was added 200 μl of a 0.1 M $H_2PtCl_6$/isopropyl alcohol (IPA) solution. The flask was placed under dry nitrogen atmosphere and the IPA removed under vacuum. Then, 6.29 g of bis(dichlorosilyl)trichlorosilylmethane and 25 ml of dried benzene were added to the flask forming a solution. The solution was maintained at reflux temperature and acetylene gas fed into the solution at a rate of 90 ml per minute for 10 hours. The resulting products were vacuum distilled at 67 Pa to yield 6.36 g of 1,1,3,3-tetrachloro-2-trichlorosilyl- 1,3-disilacyclopent-4-ene (TCD-GC are 81.4%) (TCD-GC =gas chromatography using a thermal conductivity detector) and 1,1,3,3-tetrachloro-2-trichlorosilyl-1,3-disilacyclopentane (TCD-GC 4.2%) as a mixture. The structure of 1,1,3,3-tetrachloro-2-trichlorosilyl-1,3-disilacyclopent-4-ene was confirmed by $^1$H-NMR (CDCl$_3$, ppm): 1.52 (s, 1H, SiCHSi), 7.42 (s, 2H, CH=CH).

EXAMPLE 2

Hydrosilation of phenylacetylene with bis(dichlorosilyl) trichlorosilylmethane in the presence of $H_2PtCl_6$. Into the same apparatus as described in Example 1 were placed 138 μl of 0.1 M $H_2PtCl_6$/IPA and the IPA removed under vacuum. Into the flask were add 4.96 g of bis(dichlorosilyl) trichlorosilylmethane and 25 ml of dried benzene to form a mixture. The mixture was heated to reflux and 2.55 ml of phenylacetylene were added over 20 minutes. The resulting mixture was heated at reflux temperature, with stirring, for another 5 hours. The solvent was removed at atmospheric pressure and the residue vacuum distilled at 67 Pa. The resulting product was a mixture comprising 5.94 g of 1,1,3,3-tetrachloro-2-trichlorosilyl-4-phenyl-1,3-disilacyclopent-4-ene (TCD-GC area 46.3%) and 3,3,5,5-tetrachloro-4-trichlorosilyl-1,7-diphenyl-3,5-disilahepta-1,6-diene (TCD-GC area 42.3%). 1,1,3,3-Tetrachloro-2-trichlorosilyl-4-phenyl-1,3-disilacyclopent-4-ene =$^1$H-NMR (CDCl$_3$, ppm): 1.68 (s, 1H, SiCHSi), 7.27 (s, 1H, CHCPh), 7.36–7.60 (m, 5H, ArH). 3,3,5,5-Tetrachloro-4-trichlorosilyl-1,7-diphenyl-3,5-disilahepta-1,6-diene =$^1$H-NMR (CDCl$_3$, ppm): 1.98 (s, 1H, SiCHSi), 6.12 (d, 2.4 Hz, 2H, CH=CHPh), 7.13–7.33 (m, 7H, CH=CHArH).

EXAMPLE 3

Hydrosilation of diphenylacetylene with bis (dichlorosilyl)trichlorosilylmethane in the presence of $H_2PtCl_6$/IPA. Into the same apparatus as described in Example 1 were placed 0.60 g of diphenylacetylene, 1.06 g of bis(dichlorosilyl)trichlorosilylmethane, 31 μl of 0.1 M $H_2PtCl_6$/IPA, and 25 ml of dried benzene forming a mixture. The resulting mixture, with stirring, was refluxed for 5 hours and then the solvent removed at atmospheric pressure. The residue was vacuum distilled at 67 Pa to yield a mixture comprising 1.42 g of 1,1,3,3-tetrachloro-2-trichlorosilyl-4,5-diphenyl-1,3-disilacyclopentane (TCD-GC area 71.2%) and 3,3,5,5-tetrachloro-4-trichlorosilyl-1,2,6,7-tetraphenyl-3,5-disilahepta-1,6-diene (TCD-GC area 5.9%). 1,1,3,3-Tetrachloro-2-trichlorosilyl-4,5-diphenyl-1,3-disilacyclopentane=$^1$H-NMR (CDCl$_3$, ppm): 1.82 (s, 1H, SiCHSi), 3.35–3.44 (m, 2H, CHPh), 7.06–7.18 (m, 5H, ArH).

EXAMPLE 4

Hydrosilation of acetylene with bis(dichlorosilyl) trichlorosilylmethane in the presence of Pt(C$_2$H$_4$)(PPh$_3$)$_2$. Into the same apparatus as described in Example 1 were placed 0.103 g of Pt(C$_2$H$_4$)(PPh$_3$)$_2$, 2.99 g of bis (dichlorosilyl)trichlorosilylmethane, and 20 ml of dried benzene forming a mixture. The mixture was brought to reflux and acetylene gas was blown into the mixture at 90 ml per minute for 4 hours. The mixture was vacuum distilled at 67 Pa to yield a mixture comprising 2.02 g of 1,1,3,3-tetrachloro-2-trichlorosilyl-1,3-disilacyclopent-4-ene (TCD-GC area 50.8%).

EXAMPLE 5

Hydrosilation of phenylacetylene with bis(dichlorosilyl) trichlorosilylmethane in the presence of Pt(C$_2$H$_4$)(PPh$_3$)$_2$. Into the same apparatus as described in Example 1 were add 0.99 g of bis(dichlorosilyl)trichlorosilylmethane, 0.101 g of Pt(C$_2$H$_4$)(PPh$_3$)$_2$, and 25 ml of dried benzene forming a mixture. To this mixture at reflux was added 0.32 ml of phenylacetylene over a 10 minute period. The resulting mixture was stirred for an additional 15 hours at reflux temperature and then the solvent removed. The residue was vacuum distilled at 67 Pa to give a mixture comprising 0.58 g of 1,1,3,3-tetrachloro-2-trichlorosilyl-4-phenyl-1,3-disilacyclopent-4-ene (TCD-GC area 43.9%).

EXAMPLE 6

Hydrosilation of diphenylacetylene with bis (dichlorosilyl)trichlorosilylmethane in the presence of Pt(C$_2$H$_4$)(PPh$_3$)$_2$. Into the same apparatus as described in Example 1 were added 0.99 g of bis(dichlorosilyl) trichlorosilylmethane, 0.102 g of Pt(C$_2$H$_4$)(PPh$_3$)$_2$, and 25 ml of dried benzene to form a mixture. To this mixture at reflux was added 0.52 g of diphenylacetylene in 10 ml of benzene over a 30 minute period. The resulting mixture was stirred for an additional 18 hours and then the solvent remove at atmospheric pressure. The residue was vacuum distilled at 67 Pa to yield a mixture comprising 0.61 g of 1,1,3,3-tetrachloro-2-trichlorosilyl-4,5-diphenyl-1,3-disilacyclopentane (TCD-GC area 13.8%).

EXAMPLE 7

Hydrosilation of acetylene with bis(dichlorosilyl) trichlorosilylmethane in the presence of Pd(PPh$_3$)$_4$. Into the same apparatus as described in Example 1 were added 1.01 g of bis(dichlorosilyl)trichlorosilylmethane, 0.103 g of Pd(PPh$_3$)$_4$, and 25 ml of dried benzene to form a mixture. Acetylene gas was blown into the mixture at a rate of 90 ml per minute for 3 hours. The resulting mixture was vacuum distilled at 67 Pa to yield a mixture comprising 0.89 g of 1,1,3,3-tetrachloro-2-trichlorosilyl-1,3-disilacyclopent-4-ene (TCD-GC area 50.3%).

EXAMPLE 8

Hydrosilation of phenylacetylene with bis(dichlorosilyl) trichlorosilylmethane in the presence of Pd(PPh$_3$)$_4$. Into the same apparatus as described in Example 1 were added 1.0 g of bis(dichlorosilyl)trichlorosilylmethane, 0.102 g of Pd(PPh$_3$)$_4$, and 25 ml of dried benzene to form a mixture. The mixture was brought to reflux temperature and 0.32 ml of phenylacetylene added over a 10 minute period. The mixture was stirred at reflux temperature for an additional 8 hours and then the solvent removed at atmospheric pressure. The residue was vacuum distilled at 67 Pa to yield a mixture comprising 0.348 g of 1,1,3,3-tetrachloro-2-trichlorosilyl-4-phenyl-1,3-disilacyclopent-4-ene (TCD-GC area 43.9%).

EXAMPLE 9

Hydrosilation of diphenylacetylene with bis (dichlorosilyl)trichlorosilylmethane in the presence of $Pd(PPh_3)_4$. Into the same apparatus as described in Example 1 were add 0.98 g of bis(dichlorosilyl)trichlorosilylmethane, 0.101 g of $Pd(PPh_3)_4$, and 25 ml of dried benzene to form a mixture. The mixture was brought to reflux temperature and 0.52 g of diphenylacetylene in 10 ml of benzene were added over a 30 minute period. The mixture was stirred at reflux temperature for an additional 18 hours and then the solvent removed at atmospheric pressure. The residue was vacuum distilled to yield a mixture comprising 0.417 g of 1,1,3,3-tetrachloro-2-trichlorosilyl-4,5-diphenyl-1,3-disilacyclopentane (TCD-GC area 25%).

Example 10

Hydrosilation of acetylene with tris(dichlorosilyl) methane in the presence of $H_2PtC_6$. Into the same apparatus as described in Example 1 were placed 220 μl of a 0.1 M $H_2PtCl_6$/IPA solution and the flask placed under a dry nitrogen atmosphere. The IPA was removed from the flask under vacuum and 5.31 g of tris(dichlorosilyl)methane and 30 ml of dried benzene added to form a mixture. Acetylene gas was blown into the mixture at a rate of 90 ml per minute for 8 hours. The resulting mixture was vacuum distilled at 67 Pa to yield a mixture comprising 4.51 g of 1,1,3,3-tetrachloro-2-dichlorosilyl-1,3-disilacyclopent-4-ene (TCD-GC area 31.7%) and 3,3,5,5-tetrachloro-4-dichlorosilyl-3,5-disilahepta-1,6-diene (TCD-GC area 8.6%). 1,1,3,3-Tetrachloro-2-dichlorosilyl-1,3-disilacyclopent-4-ene =$^1$H-NMR ($CDCl_3$, ppm):1.33 (d, 3.9 Hz, 1H, SiCHSi), 5.73 (d, 3.9 Hz, 1H, SiH), 7.43 (s, 2H, CH=CH).

Example 11

Hydrosilation of diphenylacetylene with tris (dichlorosilyl)methane in the presence of $H_2PtCl_6$/IPA. Into the same apparatus as described in Example 1 were place 3.39 g of diphenylacetylene, 5.91 g of tris(dichlorosilyl) methane, 40 ml of dried benzene, and 100 μl of a 0.1 M $H_2PtCl_6$/IPA solution to form a mixture. The mixture was stirred for 5 hours at reflux temperature and then the solvent removed at atmospheric pressure. The residue was vacuum distilled at 67 Pa to yield a mixture comprising 7.51 g of 1,1,3,3-tetrachloro-2-dichlorosilyl-4,5-diphenyl-1,3-disilacyclopentane (TCD-GC area of 12.3%) and 1,1,3,3 -tetrachloro-2-(1,2-dichloro-2,3-diphenyl- 1 -sila-2-propenyl)-4,5-diphenyl-1,3-disilacyclopentane (TCD-GC area 74%). 1,1,3,3-Tetrachloro-2-dichlorosilyl 4,5-diphenyl-1,3-disilacyclopentane=$^1$H-NMR ($CDCl_3$, ppm): 1.72 (d, 3.4 Hz, 1H, SiCHSi), 3.47–3.53 (m, 2H, CHPh), 5.8 (d, 3.5 Hz, 1H, SiH), 7.15–7.28 (m, 10 H, ArH). 1,1,3,3-Tetrachloro-2-(1,2-dichloro-2,3-diphenyl-1 -sila-2-propenyl)-4,5-diphenyl-1,3-disilacyclopentane=$^1$H-NMR ($CDCl_3$, ppm): 1.73(s, 1H, SiCHSi), 3.52–3.55 (m, 2H, CHPh), 7.12–7.50 (m, 21H, C=CHPh and ArH).

EXAMPLE 12

Hydrosilation of acetylene with bis(dichlorosilyl)methane in the presence of $H_2PtCl_6$. Into the same apparatus as described in Example 1 were placed 125 μl of a 0.1 M $H_2PtCl_6$/IPA solution under a dry nitrogen atmosphere and the IPA removed under vacuum. Into the flask were added 3.01 g of bis(dichlorosilyl)methane and 20 ml of dried benzene. The flask content was heated to reflux temperature and acetylene gas was blown into the content at a rate of 90 ml/min for 3 hours. The reaction products were vacuum distilled at 67 Pa to yield a mixture comprising 1.99 g of 1,1,3,3-tetrachloro-1,3-disilacyclopent-4-ene (TCD-GC area 3.6%); 1,1,3,3-tetrachloro-1,3-disilacyclopentane (TCD-GC area 47.4%); 1,1,3,3,6,6,8,8-octachloro-1,3,6,8-tetrasilaoctane (TCD-GC area 17.2%); and 1,1,3,3,6,6,8,8, 11,11,13,13-dodecachloro-1,3,6,8,11,13-hexasilatridecane (TCD-GC area 8.6%). 1,1,3,3-Tetrachloro-1,3-disilacyclopent-4-ene=$^1$H-NMR ($CDCl_3$, ppm): 1.14 (s, 2H, $SiCH_2Si$), 7.36 (s, 2H, CH=CH); 1,1,$^{3,3}$-tetrachloro-1,3-disilacyclopentane =$^1$H-NMR ($CDCl_3$, ppm): 1.12 (s, 2H, $SiCH_2Si$), 1.50 (s, 4H, $CH_2CH_2$); and 1,1,3,3,6,6,8,8-octachloro-1,3,6,8-tetrasilaoctane=$^1$H-NMR ($CDCl_3$, ppm): 1.41–150 (m, 8H, $SiCH_2SiCH_2CH_2SiCH_2Si$), 5.71 (s, 2H, SiH).

EXAMPLE 13

Hydrosilation of acetylene with bis(dichlorosilyl)methane in the presence of $H_2PtCl_6$/$PPh_3$. Into the same apparatus as described in Example 1 were placed 235 μl of 0.1 M $H_2PtCl_6$/IPA, the flask was purged with dry nitrogen and the IPA removed under vacuum. Into the flask were added 10 g of bis(dichlorosilyl)methane, 235 μl of 0.1 M $PPh_3$/benzene solution, and 20 ml of dried benzene. Acetylene gas was blown into the flask content at a rate of 90 ml/min for 10 hours. The products were vacuum distilled at 67 Pa to yield a mixture comprising 8.35 g of 1,1,3,3-tetrachloro-1,3-disilacyclopent-4-ene (TCD-GC area 22.4%); 1,1,3,3-tetrachloro-1,3-disilacyclopentane (TCD-GC area 27.4%), and 1,1,3,3,6,6,8,8-octachloro-1,3,6,8-tetrasilaoctane (TCD-GC area 22.9%).

EXAMPLE 14

Hydrosilation of acetylene with bis(dichlorosilyl)methane in the presence of $Pt((CH_2=CHSiMe_2)_2O)_2$. Into the same apparatus as described in Example 1 were placed 18 μl of $Pt((CH_2=CHSiMe_2)_2O)_2$ in 1,1,3,3-tetramethyl-1,3-divinyl-1,3-disiloxane (4 weight percent Pt) and 20 ml of dried benzene. Acetylene gas was blown into the flask at 90 ml/min for 5 hours. The products were vacuum distilled at 0.5 torr to yield a mixture comprising 3.32 g of 1,1,3,3-tetrachloro-1,3-disilacyclopent-4-ene (TCD-GC) area 6.2%); 1,1,3,3-tetrachloro-1,3-disilacyclopentane (TCD-GC area 47.9%); and 1,1,3,3,6,6,8,8-octachloro-1,3,6,8-tetrasilaoctane (TCD-GC area 27.1 %).

EXAMPLE 15

Hydrosilation of acetylene with bis(dichlorosilyl)methane in the presence of $RhCl(PPh_3)_3$. Into the same apparatus as described in Example 1 were placed 1.02 g of bis (dichlorosilyl)methane, 0.102 g of $RhCl(PPh_3)_3$, and 20 ml of dried benzene. Acetylene gas was blown into the flask at 90 ml/min for 2 hours. The products were vacuum distilled at 67 Pa to yield a mixture comprising 0.61 g of 1,1,3,3-tetrachloro-1,3-disilacyclopent-4-ene (TCD-GC area 3.7%) and 1,1,3,3-tetrachloro-1,3-disilacyclopentane (TCD-GC area 35.6%).

EXAMPLE 16

Hydrosilation of acetylene with bis(dichlorosilyl)methane in the presence of $Pt(CH_2=CH)(PPh_3)_2$. Into the same apparatus as described in Example 1 were placed 0.89 g of bis(dichlorosilyl)methane, 0.06 g of Pt(CH$_2$=CH)(PPh$_3$)$_2$, and 20 ml of dried benzene. Acetylene gas was blown into the flask at 90 ml/min for 3 hours. The products were vacuum distilled at 67 Pa to yield a mixture comprising 0.26 g of 1,1,3,3-tetrachloro-1,3-disilacyclopent-4-ene (TCD-GC area 32.1%) and 1,1,3,3-tetrachloro-1,3-disilacyclopentane (TCD-GC area 7.5%).

EXAMPLE 17

Hydrosilation of acetylene with bis(dichlorosilyl)methane in the presence of Pd(PPh$_3$)$_4$. Into the same apparatus as described in Example 1 were placed 10 g of bis(dichlorosilyl)methane, 0.103 g of Pd(PPh$_3$)$_4$, and 20 ml of dried benzene. Acetylene gas was blown into the flask at 90 ml/min for 3 hours. The products were vacuum distilled at 67 Pa to yield a mixture comprising 8.29 g of 1,1,3,3-tetrachloro-1,3-disilacyclopent-4-ene (TCD-GC area 55.2%); 3,3,5,5-tetrachloro-3,5-disilapent-1-ene (TCD-GC area 12.7%); 1,1,3,3-tetrachloro-1,3-disilacyclopentane (TCD-GC area 5.3%); and 1,1,3,3,6,6,8,8-octachloro-1,3,6,8-tetrasilaoctane (TCD-GC area 0.3%).

EXAMPLE 18

Hydrosilation of phenylacetylene with bis(dichlorosilyl)methane in the presence of H$_2$PtCl$_6$. Into the same apparatus as described in Example 1 were placed 25 µl of 0.1 M H$_2$PtCl$_6$/IPA under nitrogen and the isopropyl alcohol was removed. Then 4.95 g of bis(dichlorosilyl)methane, 20 ml of dried benzene, and 2.5 ml of phenylacetylene were added to the flask and the flask content refluxed for 2 hours. The solvent was removed from the flask at atmospheric pressure and the products distilled at 67 Pa to yield a mixture comprising 3,3,5,5-tetrachloro-1-phenyl-3,5-disilapent-1-ene (TCD-GC area 61.3%) and 3,3,5,5-tetrachloro-1,7-diphenyl-3,5-disilahepta-1,6-diene (TCD-GC area 28.1%). 3,3,5,5-Tetrachloro-1-phenyl-3,5-disilapent-1-ene=$^1$H-NMR (CDCl$_3$, ppm): 1.45 (s, 2H, SiCH$_2$Si), 5.71 (s, 1H, SiH), 6.45 (d, J=18.8Hz, 2H, SiCH=CHPh), 7.26–7.53 (m, 7H, CHArH); 3,3,5,5-tetrachloro-1,7-diphenyl-3,5-disilahepta-1,6-diene=$^1$H-NMR (CDCl$_3$, ppm): 1.43 (s, 2H, SiCH$_2$Si), 6.18 (s, 2H, SiCH=CHPh), 7.27–7.47 (m, 7H, CHArH).

Example 19

Hydrosilation of phenylacetylene with bis(dichlorosilyl)methane in the presence of H$_2$PtCl$_6$/THF. Into the same apparatus as described in Example 1 were added 1 g of bis(dichlorosilyl)methane, 20 µl of 0.1 M H$_2$PtCl$_6$ in THF (tetrahydrofuran) solution, and 20 ml of dried benzene. The flask content was heated to reflux and 0.52 ml of phenylacetylene was added over a ten minute period. The flask content was refluxed, with stirring, for another 8 hours and then the solvent removed at atmospheric pressure. The products were vacuum distilled at 67 Pa to give a mixture comprising 1.66 g of 3,3,5,5-tetrachloro-1-phenyl-3,5-disilapenta-1-ene (TCD-GC area 27.3%) and 3,3,5,5-tetrachloro-1,7-diphenyl-3,5-disilahepta-1,6-diene (TCD-GC area 26.4%).

Example 20

Hydrosilation of phenylacetylene with bis(dichlorosilyl)methane in the presence of Pt((CH$_2$=CHSiMe$_2$)$_2$O)$_2$. Into the same apparatus as described in Example 1 were added 0.99 g of bis(dichlorosilyl)methane, 20 µl Pt((CH$_2$=CHSiMe$_2$)$_2$O)$_2$ in 1,1,3,3-tetramethyl-1,3-divinyl-1,3-disiloxane (4 weight percent Pt), and 20 ml of dried benzene. The flask content was heated to reflux and 0.52 ml of phenylacetylene was added over a 10 minute period. The flask content was refluxed, with stirring, for another 2 hours and then the solvent removed at atmospheric pressure. The products were vacuum distilled at 67 Pa to give a mixture comprising 1.05 g of 3,3,5,5-tetrachloro-1-phenyl-3,5-disilapent-1-ene (TCD-GC area 18.9%) and 3,3,5,5-tetrachloro-1,7-diphenyl-3,5-disilahepta-1,6-diene (TCD-GC area 74.1%).

Example 21

Hydrosilation of phenylacetylene with bis(dichlorosilyl)methane in the presence of RhCl(PPh$_3$)$_3$. Into the same apparatus as described in Example 1 were added 0.99 g of bis(dichlorosilyl)methane, 0.102 g of RhCl(PPh$_3$)$_3$, and 20 ml of dried benzene. The flask content was heated to reflux and 0.52 ml of phenylacetylene was added over a 10 minute period. The flask content was refluxed, with stirring, for another 2 hours and then the solvent removed at atmospheric pressure. The products were vacuum distilled at 67 Pa to give a mixture comprising 0.9 g of 3,3,5,5-tetrachloro-1-phenyl-3,5-disilapent-1-ene (TCD-GC area 5.5%) and 3,3,5,5-tetrachloro-1,7-diphenyl-3,5-disilahepta-1,6-diene (TCD-GC area 66.5%).

EXAMPLE 22

Hydrosilation of phenylacetylene with bis(dichlorosilyl)methane in the presence of Pd(PPh$_3$)$_4$. Into the same apparatus as described in Example 1 were added 1 g of bis(dichlorosilyl)methane, 0.101 g of Pd(PPh$_3$)$_4$, and 20 ml of dried benzene. The flask content was heated to reflux and 0.52 ml of phenylacetylene was added over a ten minute period. The flask content was refluxed, with stirring, for another hours and then the solvent removed at atmospheric pressure. The products were vacuum distilled at 67 Pa to give a mixture comprising 0.89 g of 1,1,3,3-tetrachloro-4-phenyl-1,3-disilacyclopent-4-ene (TCD-GC area 48.2%) and 3,3,5,5-tetrachloro-1,7-diphenyl-3,5-disilahepta-1,6-diene (TCD-GC area6%).

EXAMPLE 23

Hydrosilation of diphenylacetylene in the presence Into the same apparatus as described in Example 1 were added 6.1 g of bis(dichlorosilyl)methane, 6.1 g of diphenylacetylene, 28.3 µl of 0.1 M H$_2$PtCl$_6$/IPA, and 20 ml of dried benzene. The flask content was refluxed, with stirring, for 12 hours and then the solvent removed at atmospheric pressure. The products were vacuum distilled at 67 Pa to give a crude product mixture. Crystallization from benzene gave 7.83 g of 1,1,3,3-tetrachloro-4,5-diphenyl-1,3-disilacyclopentane (yield 71 %) and 0.7 g of 3,3,5,5-tetrachloro-1,2,6,7-tetraphenyl-3,5-disilahepta-1,6-diene (yield 4%). 1,1,3,3-Tetrachloro-4,5-diphenyl-1,3-disilacyclopentane=$^1$H-NMR (CDCl$_3$, ppm): 1.51 (s, 2H, SiCH$_2$Si), 3.50 (s, 2H, CHCH), 7.12–7.28 (m, 1OH, ArH) and 3,3,5,5-tetrachloro-1,2,6,7-tetraphenyl-3,5-disilahepta-1,6-diene=$^1$H-NMR (CDCl$_3$, ppm): 1.28 (s, 2H, SiCH$_2$Si), 7.07 (s, 1H, CHPh), 7.16–7.41 (m, 20H, ArH).

EXAMPLE 24.

Hydrosilation of diphenylacetylene with bis(dichlorosilyl)methane in the presence of H$_2$PtCl$_6$/I$_2$. Into the same apparatus as described in Example 1 were added 1 g of bis(dichlorosilyl)methane, 0.84 g of diphenylacetylene, 30 μl of 0.1 M H₂PtCl₆/THF, 30 μl of 0.1 M I₂/THF, and 25 ml of dried benzene. The flask content was refluxed, with stirring, for 15 hours and then the solvents removed at atmospheric pressure. The products were distilled at 67 Pa to give a mixture comprising 1.73 g of 1,1,3,3-tetrachloro-4,6-diphenyl-1,3-disilacyclopentane (TCD-GC area 22.7%) and 3,3,5,5-tetrachloro-1,2,6,7-tetraphenyl-3,5-disilahepta-1,6-diene (TCD-GC area 57.9%).

EXAMPLE 25

Hydrosilation of diphenylacetylene with bis(dichlorosilyl)methane in the presence of Pt((CH₂=CHSiMe₂)₂O)₂. Into the same apparatus as described in Example 1 were added 1 g of bis(dichlorosilyl) methane, 0.84 g of diphenylacetylene, 20 μl of Pt((CH₂=CHSiMe₂)₂O)₂ in 1,1,3,3-tetramethyl-1,3-divinyl-1,3-disiloxane (4 weight percent Pt), and 20 ml of dried benzene. The flask content was refluxed, with stirring, for 4 hours and then the solvent removed at atmospheric presssure. The products were distilled at 67 Pa to give a mixture comprising 0.73 g of 1,1,3,3-tetrachloro-4,5-diphenyl-1,3-disilacyclopentane (TCD-GC area 73.7%) and 3,3,5,5-tetrachloro-1,2,6,7-tetraphenyl-3,5-disilahepta-1,6-diene (TCD-GC area 13.2%).

We claim:

1. A cyclic organosilicon compound described by formula

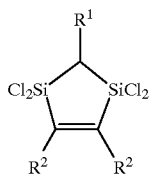

where R¹ is selected from the group consisting of hydrogen, dichlorosilyl, trichlorosilyl, methyldichlorosilyl, dimethylchlorosilyl, and trimethylsilyl, and each R² is independently selected from the group consisting of hydrogen, alkyls comprising one to about 6 carbon atoms, and aryls.

2. A cyclic organosilicon compound described by formula

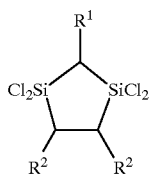

where R¹ is selected from the group consisting of hydrogen, dichlorosilyl, trichlorosilyl, methyldichlorosilyl, dimethylchlorosilyl, and trimethylsilyl, and each R² is independently selected from the group consisting of hydrogen, alkyl comprising one to about 6 carbon atoms, and aryls.

3. A linear organosilicon compound described by formula

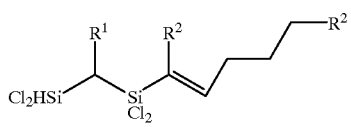

where R¹ is selected from the group consisting of hydrogen, dichlorosilyl, trichlorosilyl, methyldichlorosilyl, dimethylchlorosilyl, and trimethylsilyl, and each R² is independently selected from the group consisting of hydrogen, alkyls comprising one to about 6 carbon atoms, and aryls.

4. A linear organosilicon compound described by formula

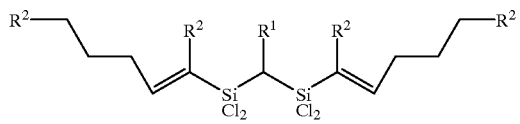

where R¹ is selected from the group consisting of hydrogen, dichlorosilyl, trichlorosilyl, methyldichlorosilyl, dimethylchlorosilyl, and trimethylsilyl, and each R² is independently selected from the group consisting of hydrogen, alkyls comprising one to about 6 carbon atoms, and aryls.

5. A method for preparing an organosilicon compound comprising effecting hydrosilation of a bis(dichlorosilyl) methane described by formula

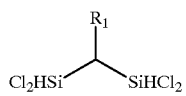

with an alkyne described by formula

in the presence of an effective amount of metallic hydrosilation catalyst, where R¹ is selected from the group consisting of hydrogen, dichlorosilyl, trichlorosilyl, methyldichlorosilyl, dimethylchlorosilyl, and trimethylsilyl, and each R² is independently selected from the group consisting of hydrogen, alkyls comprising one to about 6 carbon atoms, and aryls.

6. A method for preparing an organosilicon compound selected from the group consisting of cyclic organosilicon compounds described by formulas

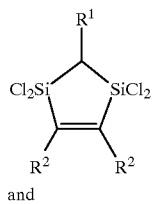

and

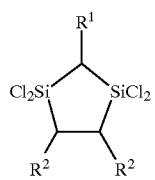

and linear organosilicon compounds described by formulas

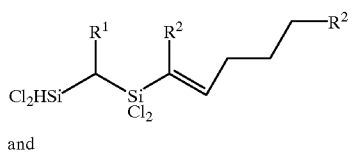

and

-continued

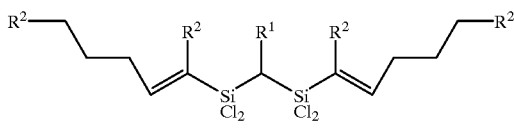

comprising effecting hydrosilation of a bis(dichlorosilyl) methane described by formula

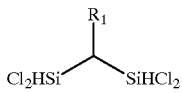

with an alkyne described by formula

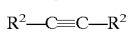

in the presence of an effective amount of metallic hydrosilation catalyst, where $R^1$ is selected from the grounp consisting of hydrogen, dichlorosilyl, trichlorosilyl, methyldichlorosilyl, dimethylchlorosilyl, and trimethylsilyl, and each $R^2$ is independently selected from the group consisting of hydrogen, alkyls comprising one to about 6 carbon atoms, and aryls.

7. A method according to claim 5, where the metallic hydrosilation catalyst is selected from the group consisting of $H_2PtCl_6$, $H_2PtCl_6/IPA$, $H_2PtCl_6/PPh_3$, $H_2PtCl_6/THF$, $H_2PtCl_6/I_2$, $Pt((CH_2=CHSiMe_2)_2O)_2$, $Pt(CH_2=CH)(PPh_3)_2$, $Pt(PPh_3)_4$, $Ni(PEt_3)_4$, $RhCl(PPh_3)_3$, and $Pd(PPh_3)_4$.

8. A method according to claim 6, where the metallic hydrosilation catalyst is selected from the group consisting of $H_2PtCl_6$, $H_2PtCl_6/IPA$, $H_2PtCl_6/PPh_3$, $H_2PtCl_6/THF$, $H_2PtCl_6/I_2$, $Pt((CH_2=CHSiMe_22O)_2$, $Pt(CH_2=CH)(PPh_3)_2$, $Pt(PPh_3)_4$, $Ni(PEt_3)_4$, $RhCl(PPh_3)_3$, and $Pd(PPh_3)_4$.

9. A cyclic organosilicon compound according to claim 1, where $R^2$ is selected from the group consisting of hydrogen and methyl.

10. A cyclic organosilicon compound according to claim 2, where $R^2$ is selected from the group consisting of hydrogen and methyl.

11. A linear organosilicon compound according to claim 3, where $R^2$ is selected from the group consisting of hydrogen and methyl.

12. A linear organosilicon compound according to claim 4, where $R^2$ is selected from the group consisting of hydrogen and methyl.

13. A method according to claim 5, where the bis(dichlorosilyl)methane is selected from the group consisting of bis(dichlorosilyl)trichlorosilylmethane and tris(dichlorosilyl)methane.

14. A method according to claim 6, where the bis(dichlorosilyl)methane is selected from the group consisting of bis(dichlorosilyl)trichlorosilylmethane and tris(dichlorosilyl)methane.

15. A method according to claim 5, where the alkyne is selected from the group consisting of acetylene, phenylacetylene, and diphenylacetylene.

16. A method according to claim 6, where the alkyne is selected from the group consisting of acetylene, phenylacetylene, and diphenylacetylene.

17. A method according to claim 5 further comprising the presence of an organic solvent.

18. A method according to claim 6 further comprising the presence of an organic solvent.

* * * * *